United States Patent [19]
Armini et al.

[11] Patent Number: 5,383,934
[45] Date of Patent: Jan. 24, 1995

[54] METHOD FOR ION BEAM TREATING ORTHOPAEDIC IMPLANT COMPONENTS

[75] Inventors: Anthony J. Armini, Manchester; Stephen N. Bunker, Wakefield, both of Mass.

[73] Assignee: Implant Sciences, Corporation, Wakefield, Mass.

[21] Appl. No.: 121,232

[22] Filed: Sep. 13, 1993

Related U.S. Application Data

[63] Continuation-in-part of Ser. No. 847,159, Mar. 4, 1992, abandoned.

[51] Int. Cl.⁶ .......................... A61F 2/30; B05D 3/06; C23C 14/48
[52] U.S. Cl. ........................ 623/16; 623/18; 623/20; 623/22; 427/529; 427/528; 427/531; 204/192.11
[58] Field of Search .......... 427/529, 528, 531; 204/192.11; 623/18, 20, 22, 16

[56] References Cited

U.S. PATENT DOCUMENTS

| | | | |
|---|---|---|---|
| 4,743,493 | 5/1988 | Sioshansi et al. | 428/217 |
| 4,855,026 | 8/1989 | Sioshansi | 204/192.11 |
| 5,037,438 | 8/1991 | Davidson | 623/18 |
| 5,123,924 | 6/1992 | Sioshansi et al. | 623/16 |
| 5,133,757 | 7/1992 | Sioshansi et al. | 623/18 |

*Primary Examiner*—Roy V. King
*Attorney, Agent, or Firm*—Iandiorio & Teska

[57] ABSTRACT

A method is disclosed for ion beam coating orthopaedic parts by ion implanting the parts with zirconium ions while the parts are immersed in an oxygen-containing background gas. A highly adherent surface layer of zirconium oxide is formed which provides a low friction, low wear graded interface for the articulating surface. The graded interface is characterized by a blackish color and a transition between pure zirconia and pure substrate material that extends over a thickness of hundreds of Angstroms. In an alternative embodiment, the thickness of the zirconia coating may be increased by also adding a simultaneous evaporation of zirconium metal on the parts.

14 Claims, 5 Drawing Sheets

METHOD FOR ION BEAM TREATING ORTHOPAEDIC IMPLANT COMPONENTS

RELATED APPLICATION

This application is a continuation-in-part of copending application Ser. No. 07/847,159, filed Mar. 4, 1992 now abandoned.

FIELD OF INVENTION

The present invention relates to a method for ion coating orthopaedic implant components with zirconium oxide on their articulating surfaces.

BACKGROUND OF INVENTION

The use of ion implantation of various elements is well known for improving the wear, friction, and other surface properties of many metal alloys. See "Surface Modification of Metals by Ion Beams", Elsevir Sequoia (1984). For alloys containing primarily the elements cobalt and chromium, both ion implanted nitrogen and titanium have been shown to improve friction and wear properties. See "Friction and Wear Behavior of Cobalt-Based Alloy Implanted with Ti or N", Mat. Res. Soc. Syrup. Proc. 27, p. 637 (1984). For orthopaedic surgical implants, cobalt-chrome alloy implanted with nitrogen has been found to improve the corrosion and subsequent wear/friction properties of the prosthetic joint. See "Medical Applications of Ion Beam Processes", Nuc. Inst. and Meth. in Physics Res. B19/20, pg. 204–208 (1987). Further, the idea of using an ion beam and physical vapor deposition simultaneously bombarding a metal surface has been in use for flat substrates. See "Properties of Aluminum Nitride Films by an Ion Beam and Vapor Deposition Method", Nucl. Inst. and Meth. in Phys. Res. B39, p. 178 (1989).

Ion implantation of nitrogen does produce some improvement in the wear and friction properties of those alloys containing predominantly cobalt and chromium when rubbing against ultra-high molecular weight polyethylene (UHMWPE) in a laboratory test, such as a pin-on-disk wear test. See. U.S. Pat. No. 5,123,924, Sioshansi et al. However, it is possible to further benefit these properties by replacing the metal surface with a continuous surface layer consisting of a ceramic material. Zirconium oxide ($ZrO_2$ or zirconia) has been found to be beneficial. See U.S. Pat. No. 5,037,438, J. Davidson et al. See also "Low Wear Rate of UHMWPE Against Zirconia Ceramic (Y-PSZ) in Comparison to Alumina Ceramic and SS316L Alloy", J. of Biomed. Mat. Res. 25, p. 813 (1991). Zirconium ions have been ion implanted into iron and steel to improve the corrosion properties. See "Surface Modification of Iron and Steel by Zirconlure or Yttrium Ion Implantation and Their Electrochemical Properties", from "Surface Modification of Metals by Ion Beams 7", Eds. F. A. Smidt, G. K. Hubler, and B. D. Sartwell, Elsevier Sequoia S. A., p. 1 (1992).

The method of growing a zirconium oxide coating on orthopaedic devices described in U.S. Pat. No. 5,037,438 requires that the prothesis be fabricated from pure zirconium metal, which is a costly process. The zirconium oxide is formed by diffusing oxygen gas into the metal at a high temperature in a furnace for a suitable period of time. The process occurs at atmospheric pressure and results in the chemical reaction of the zirconium metal workpiece and oxygen to form a surface layer of zirconium oxide.

SUMMARY OF INVENTION

It is therefore an object of this invention to provide a method for ion-coating orthopaedic prostheses with zirconium oxide.

It is a further object of this invention to provide such a method for ion-coating femoral hip ball and knee orthopaedic prostheses made from either an alloy primarily consisting of cobalt and chromium or an alloy primarily consisting of titanium or an alloy of stainless steel.

It is a further object of this invention to provide such a method for creating orthopaedic prostheses with a very low coefficient of friction on the articulating surface.

It is a further object of this invention to provide such a method for creating orthopaedic protheses having a longer useful life.

This invention results from the realization that ion implantation of zirconium ions into orthopaedic prostheses that are immersed in a low pressure, oxygen-containing gas will result in the addition of zirconium atoms to the workpiece together with their concurrent chemical reaction with oxygen to form a low-friction surface layer of zirconium oxide.

Ion implantation of zirconium is known to deposit the zirconium atoms at some depth below the surface of the workpiece. Oxygen or oxygen-containing molecules will diffuse into the workpiece during the ion bombardment. The oxygen molecules react chemically with the ion implanted zirconium atoms to form an oxide. This process may be accelerated by the energy provided by the bombarding ions. The zirconium oxide molecules gradually increase in number with dose and eventually merge into a continuous layer at or above a preferred dose depending on ion energy and angle of incidence. High energy ion bombardment of surfaces also results in the loss of surface atoms by a process called sputtering. Sputtering removes both workpiece atoms and some of the ion implanted zirconium atoms such that it is not always possible to achieve a high enough concentration of zirconium to form pure zirconium oxide. A thin layer of nearly pure zirconium oxide will often form only when the angle of incidence of the zirconium ion beam is nearly normal to the surface, because this condition results in the lowest rate of sputtering.

The ion implantation process does not deposit every implanted atom at precisely the same depth. A range of depths inevitably occurs. This is beneficial for creating a graded or blended interface between the workpiece and zirconium oxide surface coating which is not atomically abrupt but gradually varies in composition over a significant range of depths. Such a graded interface preferably varies smoothly between the composition of the pure workpiece material and nearly pure zirconium oxide at the surface and permits the physical properties between the two materials to change gradually over a range of depths. Such a graded or blended interface is beneficial for providing improved adhesion compared to conventional coatings, which are simply laid on the surface of the workpiece and which may more easily delaminate at the interface.

This invention features a process for ion beam treating a cobalt-chromium-molybdenum alloy or other metal orthopaedic implant component. The process includes immersing the implant component in an oxygen-containing gas including at least one of oxygen, ozone, water vapor and hydrogen peroxide, and providing an ion beam consisting primarily of zirconium ions to the immersed component to form an implanted zirconium oxide layer in the component. The process further includes simultaneously providing a source of either reactive zirconium or zirconium oxide, with both fluxes treating similar surface regions of the immersed component during each complete cycle of movement of the component relative to the ion beam. The component is preferably a femoral hip ball or femoral knee component. The partial pressure of the oxygen-containing gas is preferably between $5 \times 10^{-6}$ and $1 \times 10^{-3}$ Torr. The zirconium ion beam preferably has an energy of between 20 keV and 400 keV. The zirconium ion beam preferably delivers a total ion dose of between $5 \times 10^{16}$ and $5 \times 10^{18}$ ions/cm$^2$. The oxygen-containing gas is preferably oxygen. The implanted zirconium oxide layer is preferably from 50 to 5000Å thick. The process may further include maintaining the immersed component equilibrium temperature in the ion beam at from 50° C. to 600° C., which may be accomplished by adjusting the cooling to the fixture to which the component is mounted during treatment. The process may further include simultaneously moving the component relative to the ion beam about two transverse axes during implantation to create a more uniform implanted layer. The ion beam may be provided at an angle to the component. During the formation of the graded interface layer, the process may further include selection of the deposition rate per unit area for the zirconium oxide surface coating which closely equals the rate of loss caused by zirconium ion beam sputtering. For an immersed component which exhibits different average sputtering rates for different regions of it surface, the relative flux per unit area is preferably first selected to form an ion implanted zirconium oxide graded interface layer in a region of lowest average sputtering followed sequentially by selection of relative flux for regions of higher average sputtering. Also claimed is the metal oxide implanted orthopaedic implant component made by the process of the invention.

DISCLOSURE OF PREFERRED EMBODIMENTS

Other objects, features and advantages will occur to those skilled in the art from the following description of a preferred embodiment and the accompanying drawings in which.

Figure 3:
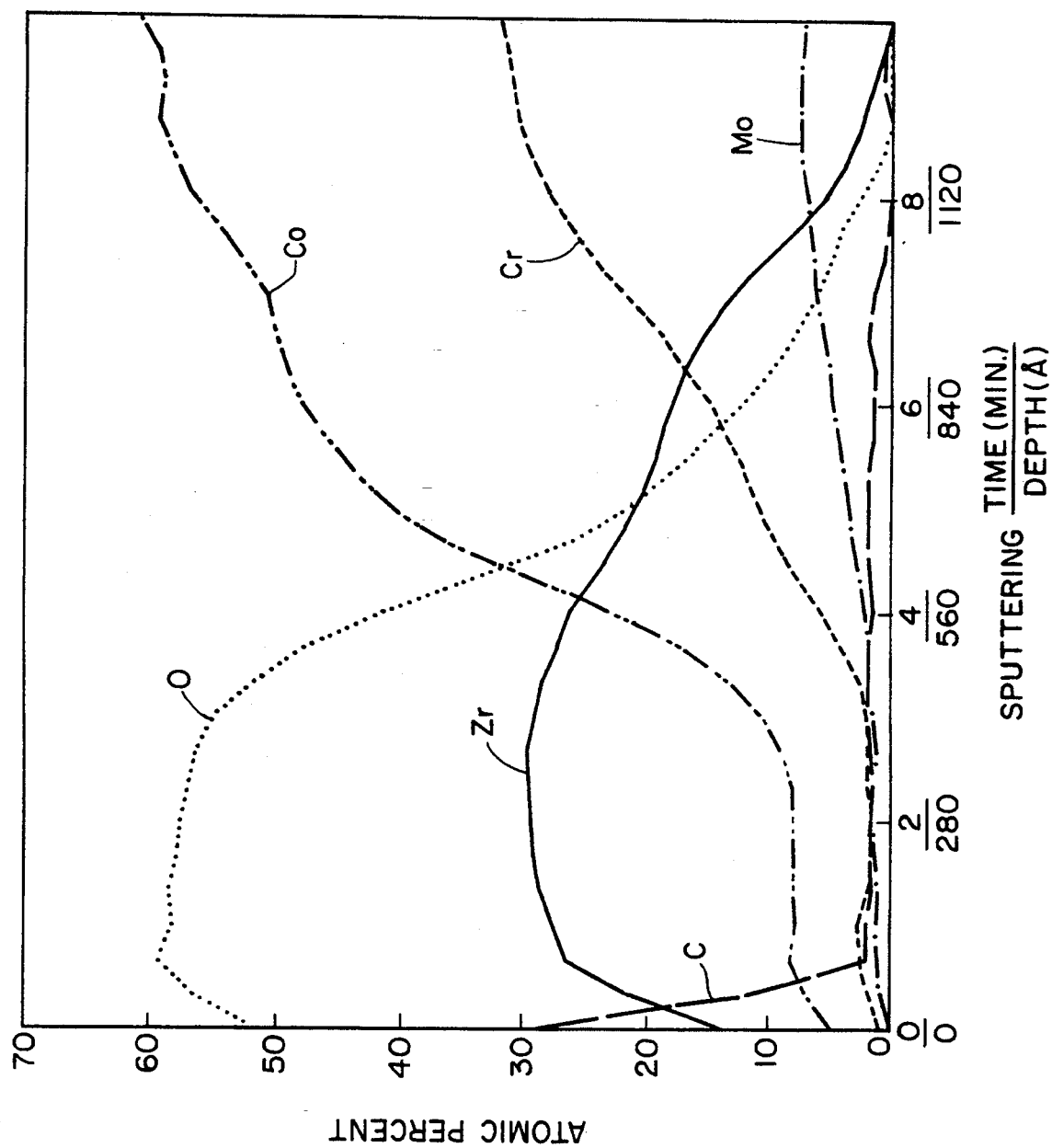
Figure 4:
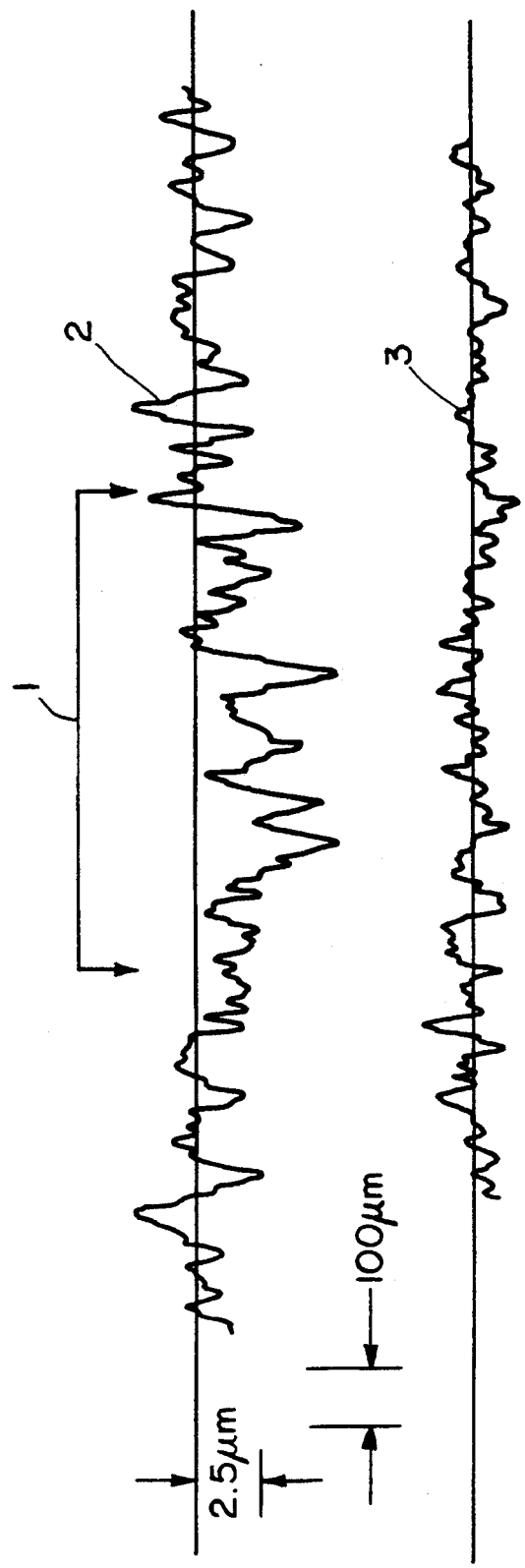

FIG. 3 is a graph of the atomic concentration of the elements found in a specimen of an alloy consisting primarily of cobalt and chromium following ion coating by the method of this invention using a zirconium ion beam at 150 keV and a dose of $2 \times 10^{17}$ atoms/cm$^2$ with an oxygen pressure of $3 \times 10^{-5}$ Torr; and FIG. 4 is a chart detailing a wear test establishing the low coefficient of friction on parts coated by the process of this invention.

This invention results from a first realization that a surface layer of an oxide ceramic of zirconium can be created; by the simultaneous bombardment of a workpiece by an ion beam consisting of zirconium while the workpiece is immersed in a low pressure gas which includes oxygen atoms. The workpiece may be an alloy composed primarily of cobalt and chromium, such as either cast ASTM-F75 alloy or wrought ASTM-F799 alloy. The workpiece may also be a surgical alloy composed primarily of titanium, such as titanium-6aluminum-4vanadium. The workpiece may also be a surgical grade of stainless steel. It is further realized that the metal ion most effective in forming zirconium oxide is zirconium. It is further realized that the energy of the bombarding ions should be in the range from 20 keV to 400 keV and preferably at 200 keV. It is further realized that the low pressure oxygen-containing gas may be composed of any one or more of the compounds of pure oxygen, water vapor, ozone, or hydrogen peroxide, with pure oxygen preferred. Other gases, such as nitrogen, may also be present and which do not contribute to the formation of the oxide. It is further realized that the partial pressure of the oxygen-containing gas or gases should be in the range from $6 \times 10^{-6}$ Torr to $1 \times 10^{-3}$ Torr and preferably at $4 \times 10^{-5}$ Torr. It is further realized that the temperature of the workpiece during ion bombardment should be in the range from 100° C. to 600° C. and preferably at 250° C.

The zirconium ion beam dose may be chosen as desired and should be in the range from $5 \times 10^{16}$ to $5 \times 10^{18}$ atoms/cm$^2$. Preferably, for a flat surface whose normal axis coincides with the direction of the ion beam, the dose is $3 \times 10^{17}$ atoms/cm$^2$ for a 150 keV zirconium ion beam. Curved or tilted surfaces may require other preferred doses, depending on the geometry. The preferred dose is needed to convert a layer to substantially all zirconium oxide.

Many useful workpieces have curved or tilted surfaces that cannot form a nearly pure ion implanted buried layer of zirconium oxide because of a high rate of sputtering by the ion beam due to the angle of incidence of the beam at the surface. This limitation may be overcome by additionally providing a source of zirconium or zirconium oxide which deposits a coating on the workpiece at a rate which closely equals the rate of loss of atoms caused by sputtering. The flux of zirconium or zirconium oxide may be provided by known methods such as high temperature evaporation, sputtering, or electron arc discharged. This coating is preferably removed by sputtering as rapidly as it is deposited, providing no net gain or loss of either the coating or workpiece materials. Such a coating rate allows atoms of the zirconium ion beam to be nearly completely retained below the surface of the workpiece without losses caused by sputtering. The concentration of ion implanted zirconium atoms below the surface can then be increased to the preferred level by selecting a dose which makes a zirconium oxide graded interface layer. The preferred rate of coating deposition depends on the geometry and is indicated visually by a blackening of the surface after sufficient zirconium ion dose is provided to form the zirconium oxide graded interface layer. An insufficient coating rate during the ion implantation of zirconium causes a silver-grey color on a polished surface, and an excessive rate causes a colored hue, such as red or green, which is characteristic of a reflection optical interference effect.

Figure 1:
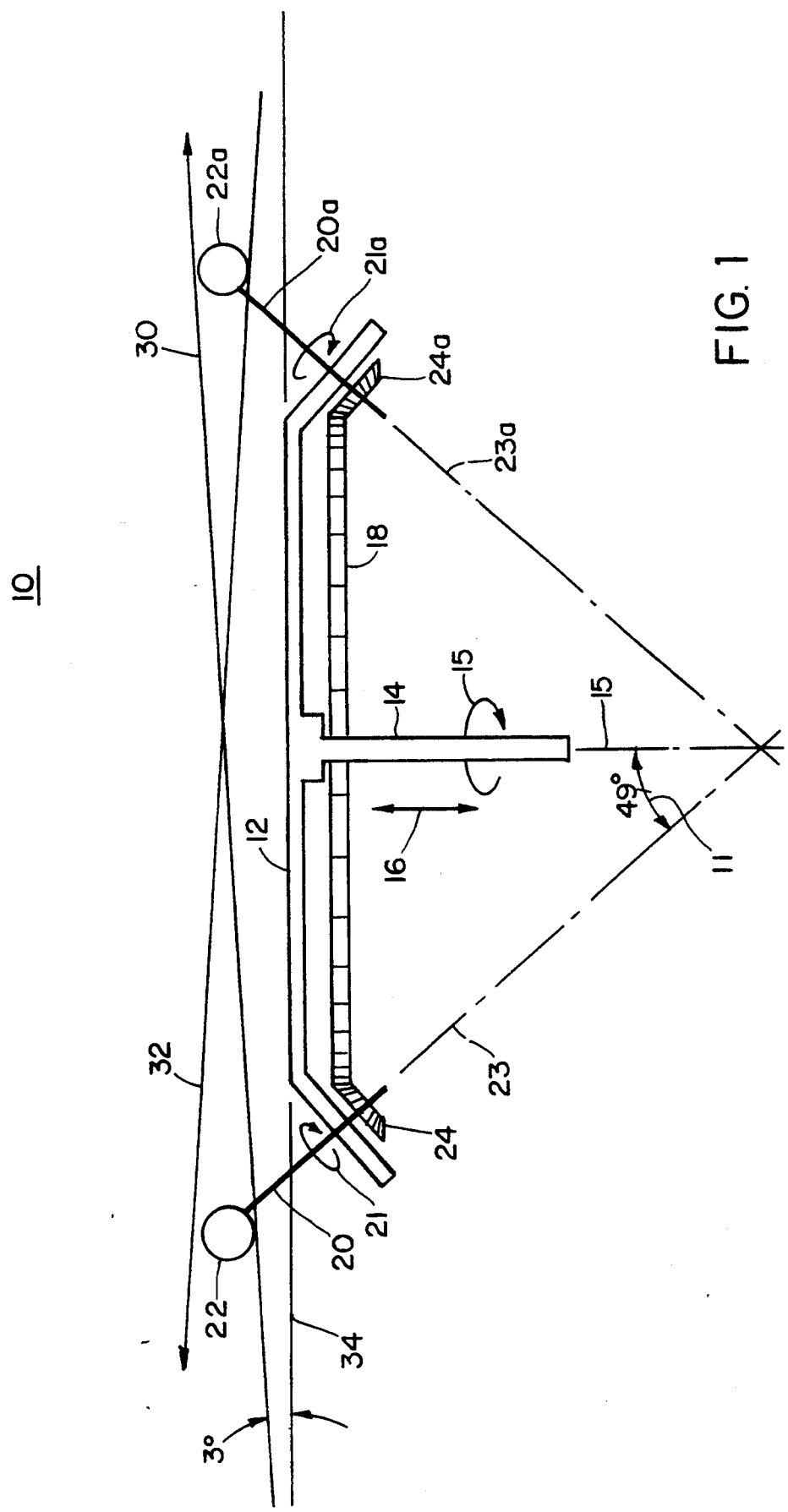
FIG. 1 is a schematic diagram of an ion implantation apparatus for accomplishing the method of this invention.

There is shown schematically in FIG. 1 ion implantation apparatus 10 as disclosed in our copending application 07/847,159, incorporated herein by reference, for extremely uniformly ion beam implanting or coating irregularly-shaped parts. Apparatus 10 includes rotatable turntable or fixture 12 fixed to rotatable shaft 14. Below turntable 12 there is a fixed disc 18 having a gear-engaging surface to act as a fixed sun gear. Parts 22, 22a to be coated, for example prosthetic hip balls, are mounted on shafts 20, 20a, respectively, to which are fixed planetary gears 24, 24a, that are engaged with the gear engaging surface of sun gear 18. When shaft 14 is rotated in the direction of arrow 15, balls 22 are caused to rotate around axis 15 as well as shaft axis 23, 23a to simultaneously rotate parts 22, 22a about two transverse axes. Preferably the angle between axis 15 and axis 23 is acute, and an angle of 49° has been found to result in extremely uniform ion treating of the surfaces of parts 22, 22a.

While the parts are rotating, they are exposed to one or more ion beams 30 and 32 that are preferably provided at a slight angle to plane 34 of fixture 12 so that the parts do not shadow each other. For implantation of prosthetic hip ball components, the beam axis is preferably approximately 3° to 10° from plane 34. The important parameter is the prevention of shadowing of the part by another. The beam angle necessary to accomplish this may be determined by drawing a line from the bottom of part 22 to the top of part 22a and determining the angle at which that line intersects plane 34. When the beam is provided at at least this angle, the part closest to the beam source will not shadow the rear part.

Figure 2A:
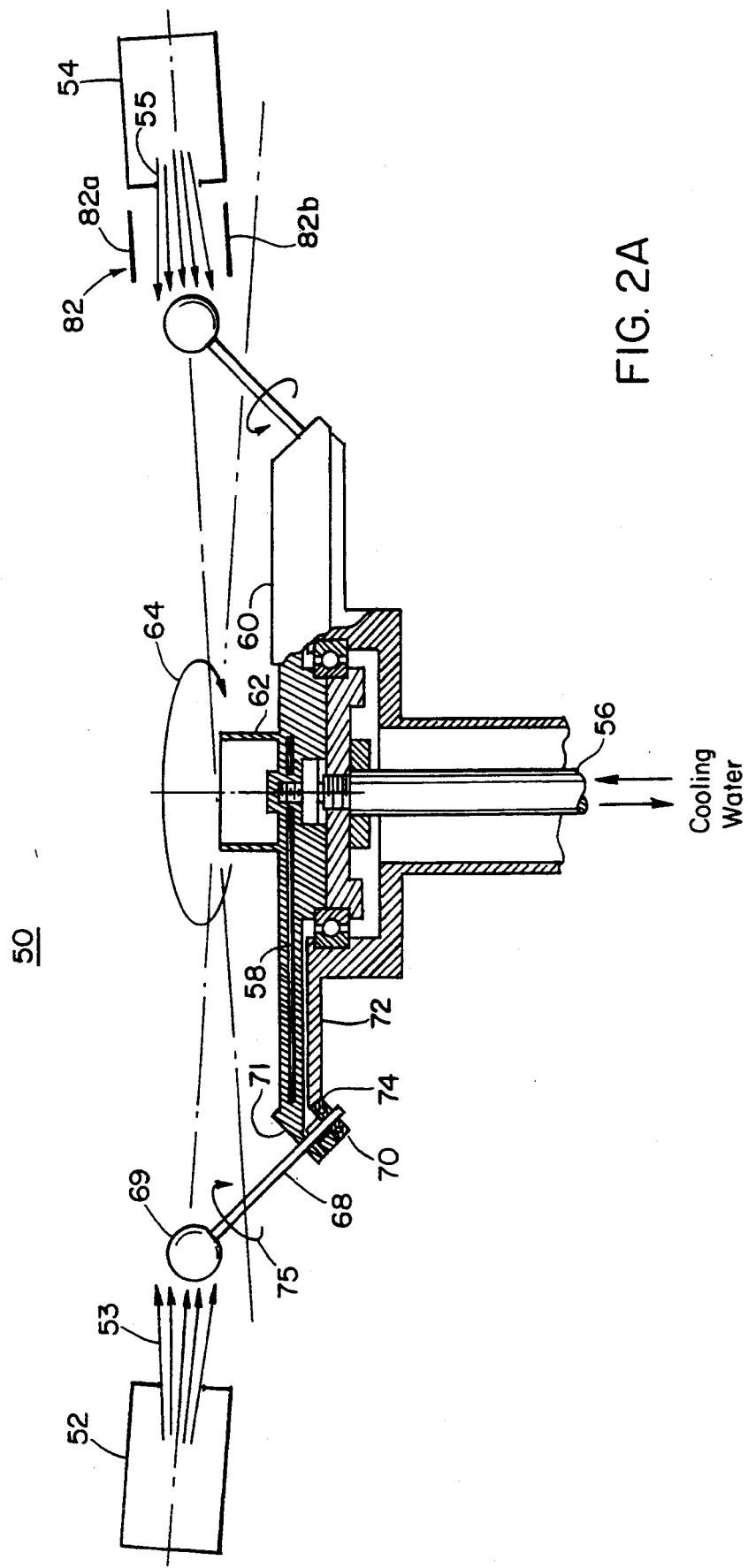
FIG. 2A is a detailed, party cross-sectional view of a preferred embodiment of the apparatus of FIG. 1.

Apparatus 50, FIG. 2A, has been successfully used for uniformly ion-beam coating prosthetic hip balls with zirconium ions on cobalt chromium alloy prostheses. Preferably, the balls are spaced as closely as possible together so that ion beam is not wasted.

Beams 53, 55, FIG. 2A, are typically approximately one inch in diameter and are preferably scanned in relation to the parts being coated by either translating fixture 60 in the direction of arrow 16, FIG. 1, or electrostatically deflecting the beams for example by using deflection mechanism 82, FIG. 2A, including plates 82a, 82b for applying a voltage gradient across the beam. Preferably, the part-holding fixture is continuously translated up and down a distance approximately equal to the height of the parts being coated to insure that the beams are uniformly scanned across the surfaces being coated.

The ion beam dose may be chosen as desired, and is preferably between about $5 \times 10^{16}$ and $5 \times 10^{18}$ ions/cm$^2$. The ion beam current density is defined as the ion beam current divided by the cross-sectional area whose normal axis is parallel to that of the direction of the ion beam. The ion beam current density is typically chosen to be between approximately 200 to 2,000 microamperes/cm$^2$ with a beam energy between about 20 keV and 400 keV. The ion beam current density is chosen as high as possible consistent with the ion beam generation equipment used so as to provide a high speed economically viable process. The total ion beam power is defined as the ion beam current times the net accelerating voltage applied to the beam. The total ion beam power divided by the total area swept out by the array of workpieces defines the ion beam power dissipation density. The ion beam power dissipation density is selected to maintain the workpieces at an average temperature between 50° C. to 600° C. during processing.

Figure 2B:
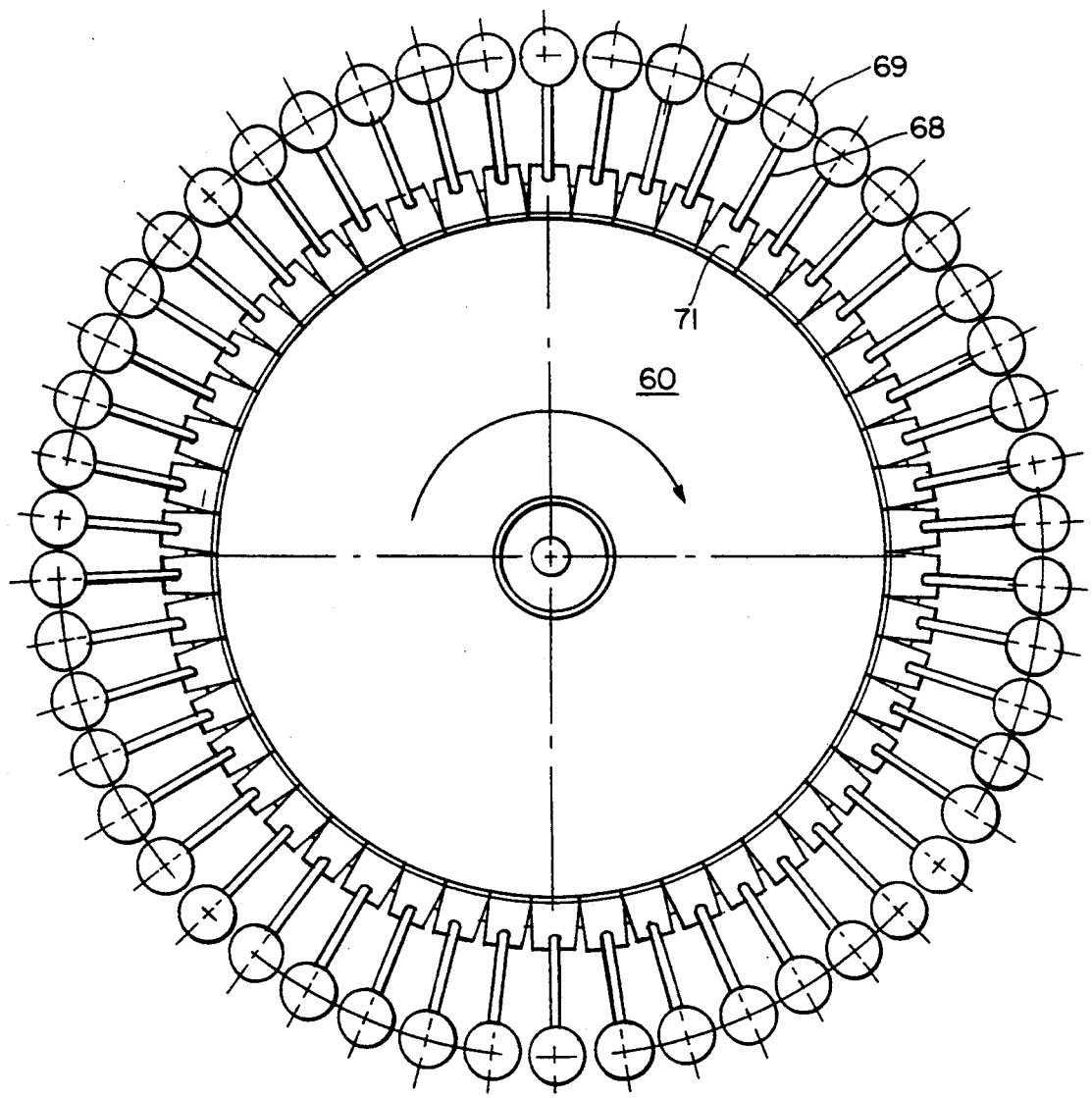
FIG. 2B is a top view of the device of FIG. 2A illustrating the close packing of the parts being coated.

A spherical workpiece, such as a femoral hip prosthesis, can be ion beam implanted with a graded interface of zirconium oxide using the apparatus of FIGS. 2A and 2B. It is realized that with said apparatus, only a limited area on a spherical workpiece can be ion beam treated to produce a graded interface of ion implanted zirconium oxide when a fixed flux per unit area of zirconium oxide coating deposition and a fixed flux per unit area of zirconium ion beam is applied. It is further realized that such a limited area consists of those regions on the spherical workpiece subjected to a similar average rate of sputtering as the spherical workpiece is manipulated to present all of its articulating surface to the zirconium ion beam and coating deposition. It is further realized that once a blackish graded interface zirconium oxide layer has formed, an increase in the coating deposition flux per unit area relative to the zirconium ion beam flux per unit area will deposit a zirconium oxide coating over the blackish graded interface zirconium oxide layer.

Therefore, an ion implanted graded interface zirconium oxide layer can be introduced into a spherical workpiece by simultaneously subjecting the surface to a zirconium oxide coating deposition flux per unit area and a zirconium ion beam flux per unit area while immersed in a partial pressure of oxygen. The total dose of zirconium ions and the fluxes per unit area are first selected to form a blackish graded interface layer in a region on the workpiece which is subjected to the lowest average rate of sputtering. If the apparatus of FIGS. 2A and 2B is employed, this region will be on the rotation axis of the spherical workpiece. After the first region is so treated, the coating deposition flux per unit area relative to the zirconium ion beam is incrementally increased to form the blackish graded interface layer in a region subjected to a higher average rate of sputtering. This process is repeated until all the desired surface regions are so treated. On a spherical workpiece a coating of zirconium oxide will accumulate on those regions that have smaller average rates of sputtering than the region currently being treated to form the blackish graded interface layer of ion implanted zirconium oxide.

It is realized that the method of forming a blackish ion implanted layer of zirconium oxide described for spherical orthopaedic workpieces may also be applied as a general method for other shapes of orthopaedic workpieces, such as femoral knee prostheses. It is further realized that other shapes of orthopaedic workpieces may require a different type of apparatus for manipulating the workpiece to ensure uniform treatment than the type shown in FIGS. 2A and 2B.

EXAMPLE I

A flat CoCr specimen was ion implanted in oxygen gas using the invention using the following process parameters:

| Ion Beam Species: | $^{90}Zr^+$ |
| --- | --- |
| Ion Beam Energy: | 150 keV |
| Ion Beam Dose: | $2 \times 10^{17}$ $Zr^+$/cm$^2$ |
| Oxygen Gas Pressure: | $2 \times 10^{-5}$ Torr |
| Beam Area: | 25 cm$^2$ |
| Beam Current: | 1 mA |
| Process Time: | 80 minutes |
| Angle of Ion Beam to Surface: | 0° |

FIG. 3 shows the resulting AES depth profile of the resulting zirconia coating.

At zero depth there is a zirconium oxide coating with little cobalt, chromium, and molybdenum. The small amount of carbon at the surface is almost always seen in ion implantation of metals and is due to absorbed carbon from the background gases in the chamber. The analysis shows that the ceramic, in this case $ZrO_2$, is essentially pure and stoichiometric to a depth of about 500Å at which point it blends into the substrate. The ordinate of this graph is the atomic percent of each constituent where the total at any depth must add to 100%. The abscissa is the depth in the substrate in sputter time in minutes (numerator) or Å (denominator). At a depth of approximately 1120Å, there is no zirconia, indicating the depth of the implantation accomplished by the process of Example I.

EXAMPLE II

A cobalt chrome alloy spherical femoral hip prosthesis was coated with zirconia using the preferred process in which the ion beam subjects the surface to a range of large rates of sputtering using the following parameter and process conditions:

(a) Blending Phase
| | |
|---|---|
| Ion Beam: | Zirconium 90 |
| Beam Current: | 0.5 mA |
| Beam Energy: | 190 keV |
| Scanned Area: | 58 cm$^2$ |
| Evaporant: | Zirconium |
| Deposition Rate: | 0.4 to 1.0Å/sec in 3 steps (determined to balance sputter rate) |
| Oxygen Pressure: | $3 \times 10^{-5}$ Torr |
| Dose at Each Step: | $2 \times 10^{17}$ Zr$^+$/cm$^2$ |
| Rotational Axis of Prosthesis: | 45° to axis of ion beam and evaporator |

(b) Growth Phase
| | |
|---|---|
| Ion Beam: | Zirconium 90 |
| Beam Current: | 200 μA (constant) |
| Beam Energy: | 36 keV (constant) |
| Scanned Area: | 58 cm$^2$ |
| Evaporant: | Zirconium |
| Deposition Rate: | 1.40Å/sec. (constant) |
| Oxygen Pressure: | $3 \times 10^{-5}$ Torr |
| Time Duration: | 2 Hours |

The resulting blackish zirconia coating was approximately 1 micron thick and blended into the substrate over approximately a 1000Å depth.

EXAMPLE III

One face of a hip ball coated according to Example I along with an uncoated CoCr ball, were subjected to a wear test sliding against an ultrahigh molecular weight polyethylene (UHMWPE) disk. The disk wear was measured after the completion of each test.

The Pin-on-Disk test parameters were:

| | |
|---|---|
| Pin Type: | 1. ZrO$_2$ coated CoCr ball |
| | 2. uncoated control CoCr ball |
| Disk Material: | UHMWPE |
| Pin Pressure: | 18 MPa |
| Sliding Velocity: | 15 cm/sec |
| Total Slide Distance: | 8.1 km |
| Total Test Time: | 15 hours |

The results of these two tests are shown in FIG. 4. These data show the depth of a typical wear groove 1 in the disks as measured with a surface profiler. Trace 3 shows the disk wear for the zirconia coated ball and trace 2 shows the disk wear due to the control ball. Six traces were taken around the circumference of each circular groove (one every 60°) and yield average wear volumes:

| | |
|---|---|
| Wear (ZrO$_2$) | <0.009 mm$^3$ |
| Wear (control) = | 0.139 ± .040 mm$^3$ |

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A process for ion beam treating a metallic orthopaedic implant component to form a zirconium oxide graded interface layer between the metallic component and a subsequently applied zirconium oxide coating, comprising:
   immersing the implant component in an oxygen containing gas at a pressure between $5 \times 10^{-6}$ and $1 \times 10^{-3}$ Torr;
   providing an ion beam of zirconium to the immersed component; and
   providing a source of zirconium vapor to the immersed component to form the interface layer of ion implanted zirconium oxide varying between the composition of pure metallic component material from beneath the surface of said metallic component to pure zirconium oxide on the surface of said metallic component.

2. The process of claim 1 further including selecting a deposition rate per unit area for the zirconium vapor during the formation of the graded interface layer which substantially equals the rate of loss of the metallic component caused by zirconium ion beam sputtering.

3. The process of claim 1 further including selecting a dose of zirconium ions to form a blackish colored zirconium oxide graded interface layer that consists essentially of zirconium atoms from the ion beam.

4. The process of claim 3 further including selecting a deposition rate per unit area for the zirconium vapor which exceeds the rate of loss of the metallic component caused by zirconium ion beam sputtering in order to form a coating of zirconium oxide over the previously formed blackish zirconium oxide graded interface layer.

5. The process of claim 1 in which the immersed component is a femoral hip ball or femoral knee prosthesis.

6. The process of claim 1 in which the immersed component is composed of an alloy consisting essentially of cobalt and chromium, or titanium, or stainless steel.

7. The process of claim 1 in which said oxygen containing gas is selected from the group consisting of oxygen, ozone, water vapor, and hydrogen peroxide vapor.

8. The process of claim 1 in which the zirconium ion beam has an energy of between 20 keV and 400 keV.

9. The process of claim 1 in which the zirconium ion beam delivers a total ion dose of between $5 \times 10^{16}$ and $5 \times 10^{18}$ ions/cm$^2$ to the immersed component.

10. The process of claim 1 in which the source of the zirconium vapor, which forms a surface coating of zirconium oxide, is provided by evaporation, sputtering, or arc discharge.

11. The process of claim 1 further including maintaining the immersed component at a temperature in the ion beam from 25° C. to 600° C.

12. The process of claim 1 further including simultaneously moving the component relative to the ion beam about two transverse axes during implantation to create a uniform graded interface layer.

13. The process of claim 3 in which the blackish zirconium oxide graded interface layer is from 50 to 5000Å thick.

14. The ion beam treated orthopaedic implant component made by the process of claim 1.

* * * * *